US007057119B2

(12) United States Patent
Larsen et al.

(10) Patent No.: US 7,057,119 B2
(45) Date of Patent: Jun. 6, 2006

(54) EGG WEIGHING APPARATUS

(75) Inventors: Hugh W. Larsen, Milford, MI (US); Douglas A. Kane, Livonia, MI (US); Robert J. Washnock, Royal Oak, MI (US)

(73) Assignee: Michigan Scientific Corp., Milford, MI (US)

( * ) Notice: Subject to any disclaimer, the term of this patent is extended or adjusted under 35 U.S.C. 154(b) by 157 days.

(21) Appl. No.: 10/760,811

(22) Filed: Jan. 20, 2004

(65) Prior Publication Data

US 2004/0149497 A1 Aug. 5, 2004

Related U.S. Application Data (60) Provisional application No. 60/441,389, filed on Jan. 20, 2003.

(51) Int. Cl.
*G01G 23/12* (2006.01)
*G01G 21/28* (2006.01)
*A01K 43/08* (2006.01)

(52) U.S. Cl. .................... 177/187; 177/175; 177/238; 209/513

(58) Field of Classification Search ........ 177/151–152, 177/175–176, 184–189, 193, 229, 238–244; 209/513
See application file for complete search history.

(56) References Cited

U.S. PATENT DOCUMENTS

| 3,948,765 | A |   | 4/1976  | Anschutz ................ 209/513 |
| 3,991,841 | A | * | 11/1976 | Crawley ................. 177/225 |
| 3,993,150 | A | * | 11/1976 | Brosh et al. ............ 177/211 |
| 4,020,686 | A | * | 5/1977  | Brendel ................. 177/229 |
| 4,065,962 | A | * | 1/1978  | Shoberg ............. 73/862.628 |
| 4,379,495 | A | * | 4/1983  | Cocks et al. ............... 177/1 |
| 4,448,085 | A | * | 5/1984  | Lee ................... 73/862.626 |
| 4,478,302 | A |   | 10/1984 | Niederer et al. ......... 177/145 |
| 4,553,619 | A | * | 11/1985 | Fujinaga ................ 177/185 |
| 4,715,457 | A | * | 12/1987 | Amacher et al. ........... 177/1 |
| 4,770,261 | A | * | 9/1988  | Yamahaka .............. 177/185 |
| 4,848,495 | A | * | 7/1989  | Hayashi ................ 177/187 |
| 4,850,443 | A | * | 7/1989  | Bergholt et al. ......... 177/188 |
| 5,488,203 | A | * | 1/1996  | Hassel et al. ........... 177/184 |

\* cited by examiner

*Primary Examiner*—Randy W. Gibson
(74) *Attorney, Agent, or Firm*—Young & Basile, P.C.

(57) ABSTRACT

A device and method for weighing eggs. The egg weighing apparatus includes a movable stem that supports an egg weighing platform. The stem is attached to a measuring device that is electronically and mechanically driven for precise measurement of an egg. The present invention uses a damper or alternatively, uses a tuned dynamic vibration absorber to yield precise measurement of an egg.

18 Claims, 7 Drawing Sheets

EGG WEIGHING APPARATUS

CROSS REFERENCE TO CO-PENDING APPLICATIONS

This Utility Application claims priority from the filing date of Jan. 20, 2003, of U.S. Provisional Application Ser. No. 60/441,389, the contents of which are incorporated herein in its entirety.

BACKGROUND

The present invention relates to an egg weighing apparatus.

The handling of shell eggs for marketing has matured into a volume production business. Chicken farms housing hundreds of thousands and even millions of egg laying chickens utilize high speed collection systems which collect the eggs laid by the chickens, washes, candles, checks the egg shells for cracks, grades the eggs generally by weight, sorts the eggs into groups according to the grade or weight and then packages the eggs for shipping.

While the grade contains several different categories, such as jumbo, large, medium, small and others, each grade is generally defined by a very small range of weights which may be set by government regulations or customer demand.

The extremely large number and the high speed of the egg handling equipment necessitates that the weighing of each egg take place quickly, typically in less than one second.

Generally, a high speed egg handling apparatus will utilize a weighing station which contains multiple scales which are capable of weighing each egg passing over the scale and generating an output signal to a computer which stores the weight with a particular egg identification to track the egg through the handling and sorting process.

Known egg weighing apparatus or scales utilize damping means to reduce the oscillations caused in the scale as each egg drops into the weighing platform or perch. Damping is usually accomplished by shearing a viscous fluid. However, optimal damping can be difficult to maintain over extended time and temperatures. Further, all of the damping fluid must be contained from loss.

In addition, the egg handling facility requires frequent washing to maintain a high level of sanitary conditions. The application of high pressure cleaning solutions or water may be used in most portions of the egg handling equipment, such as the conveyers, sorters, etc. However, the precision weighing apparatus have not heretofore been capable of being cleaned through high pressure fluid application due to the design of the scales themselves. This has necessitated gentle hand washing which slows the cleaning operation.

Thus, it would be desirable to provide an egg weighing apparatus for high speed egg handling equipment which addresses the deficiencies of previously devised egg weighing apparatus.

SUMMARY OF THE INVENTION

The present invention provides an apparatus for weighing an egg. The apparatus includes a housing, sensor means for weighing an egg, a tower mounted on the housing for supporting and surrounding the sensor means and a stem movably displaced through one open end of the tower and supporting an egg weighing platform.

The egg weighing apparatus includes a force transmission member formed of a solid body with two legs, one leg carrying bores for receiving fasteners for attaching the transmission member to a transducer, and an angularly disposed second leg attaching the transmission member to the stem.

One aspect of the invention encompasses usage of a tuned dynamic vibration absorber, wherein a mass element is attached to the force transmission member to diminish vibratory oscillation of a perch attached to the upper end of the stem, the oscillation is diminished by minimizing movement of the stem.

One end of the stem is attached to the force transmission member and the other end of the stem is attached to the egg weighing platform.

In one aspect of the invention, a water resistant sealing cap is releasably mounted on the outer surface of the stem between the tower and the egg weighing platform. The water resistant sealing cap includes a bore and the cap has a first end and a second end. The bore has a complimentary shape to the exterior shape of a collar in the tower and forms a labyrinth path through the second end of the cap.

The present invention also defines a method for weighing an egg comprising the steps of placing an egg in a weighing platform, displacing a stem connected to the weighing platform in proportion to the weight of the egg wherein such displacement generates distortion of a force transmission member coupled to the stem in a measurable strain. Then supplying the measured strain to a control means in the form of a signal proportional to the displacement of the stem.

The present invention provides a high speed egg weighing apparatus that provides the user option of using a damper or not using a damper to provide precision egg weighing. An alternative aspect of the invention that is employed when damping is not used is inclusion of a tuned dynamic vibration absorber. The tuned dynamic vibration absorber is employed to diminish vibratory oscillations, the oscillations can not exceed the pre-determined mechanical limits of the transducer. The transducer is one alternative that can be chosen for the sensing means of the present invention.

BRIEF DESCRIPTION OF THE DRAWING

The various features, advantages and other uses of the present invention will become more apparent by referring to the following detailed description and drawings in which.

DETAILED DESCRIPTION

Figure 1:
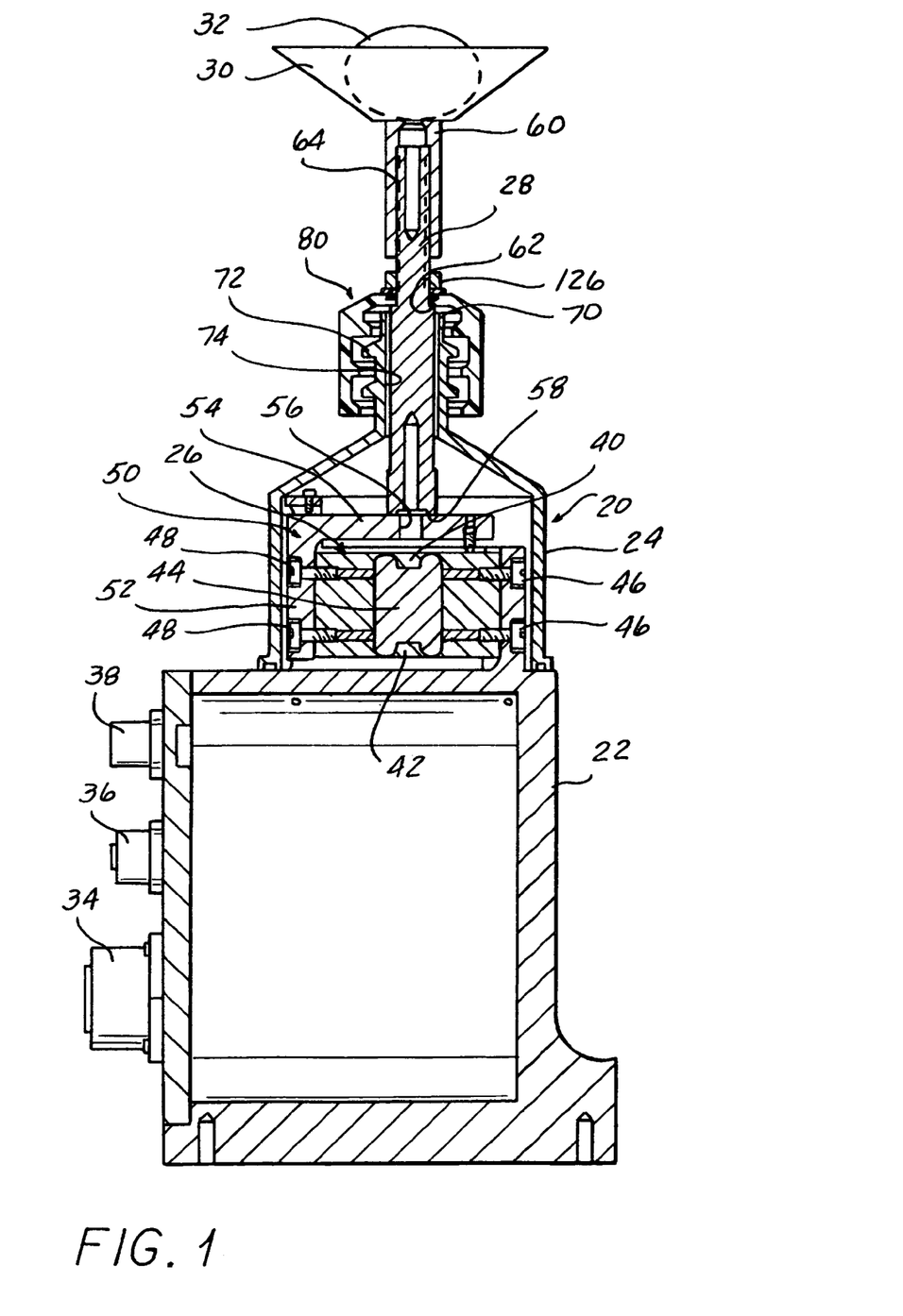
FIG. 1 is a longitudinal, cross sectional view of an egg weighing apparatus according to one aspect of the present invention.
Figure 2:
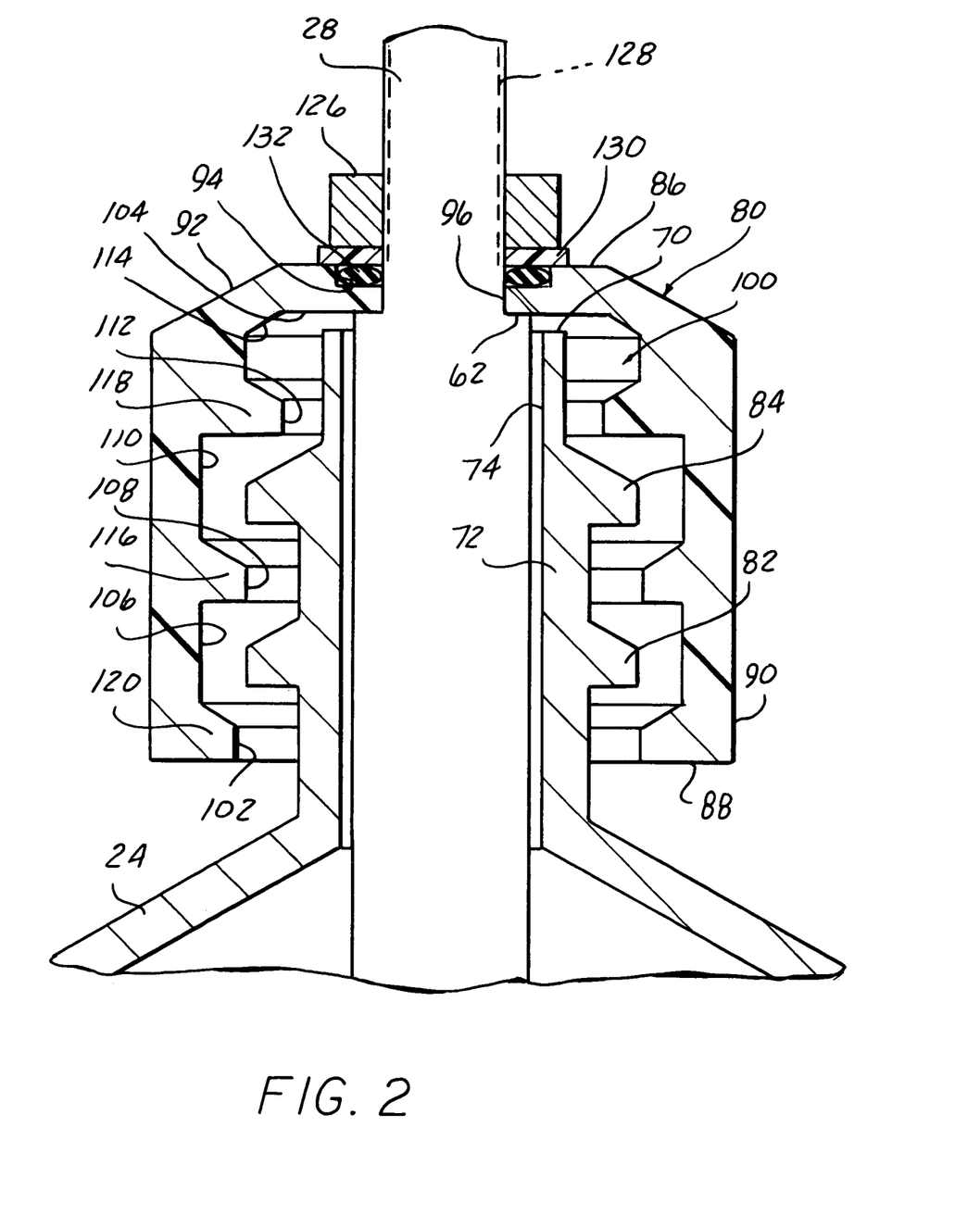
FIG. 2 is an enlarged, cross sectional view of a portion of the apparatus shown in FIG. 1.

Referring now to FIGS. 1 and 2, there is depicted an egg weighing apparatus 20 constructed according to one aspect of the present invention.

The apparatus 20 includes a base or housing 22 on which a tower 24 is mounted for supporting and surrounding a sensor means or transducer 26. A stem 28 is movably disposed through one open end of the tower 24 and supports a weighing platform or perch 30 at an upper end. The perch 30 is designed to receive an egg shown in phantom by reference number 32 during a weighing operation or cycle, with the egg 32 being transported to and from the perch 30 by means of transporting or conveying equipment, not shown.

Figure 6:
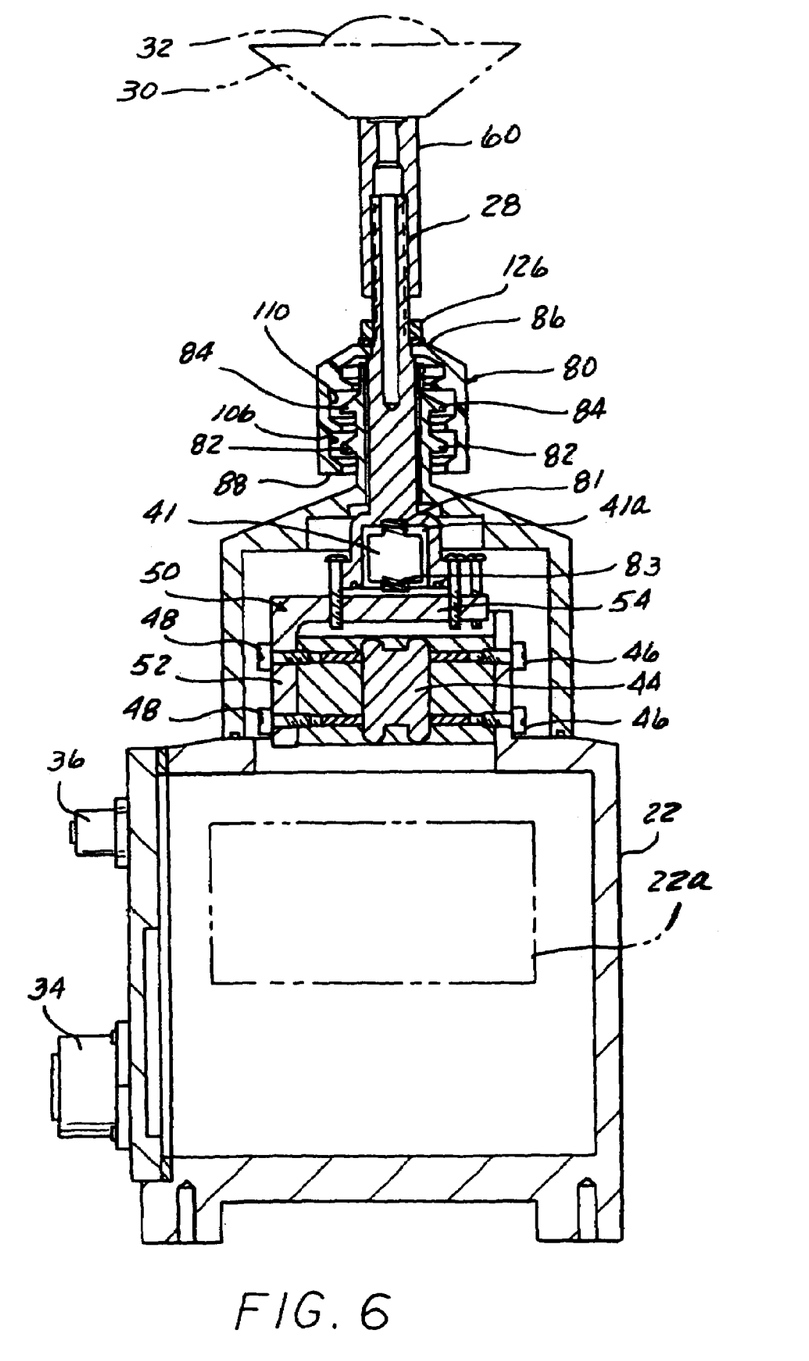
FIG. 6 is a cross sectional view of an egg weighing apparatus according to another aspect of the present invention.
Figure 7:
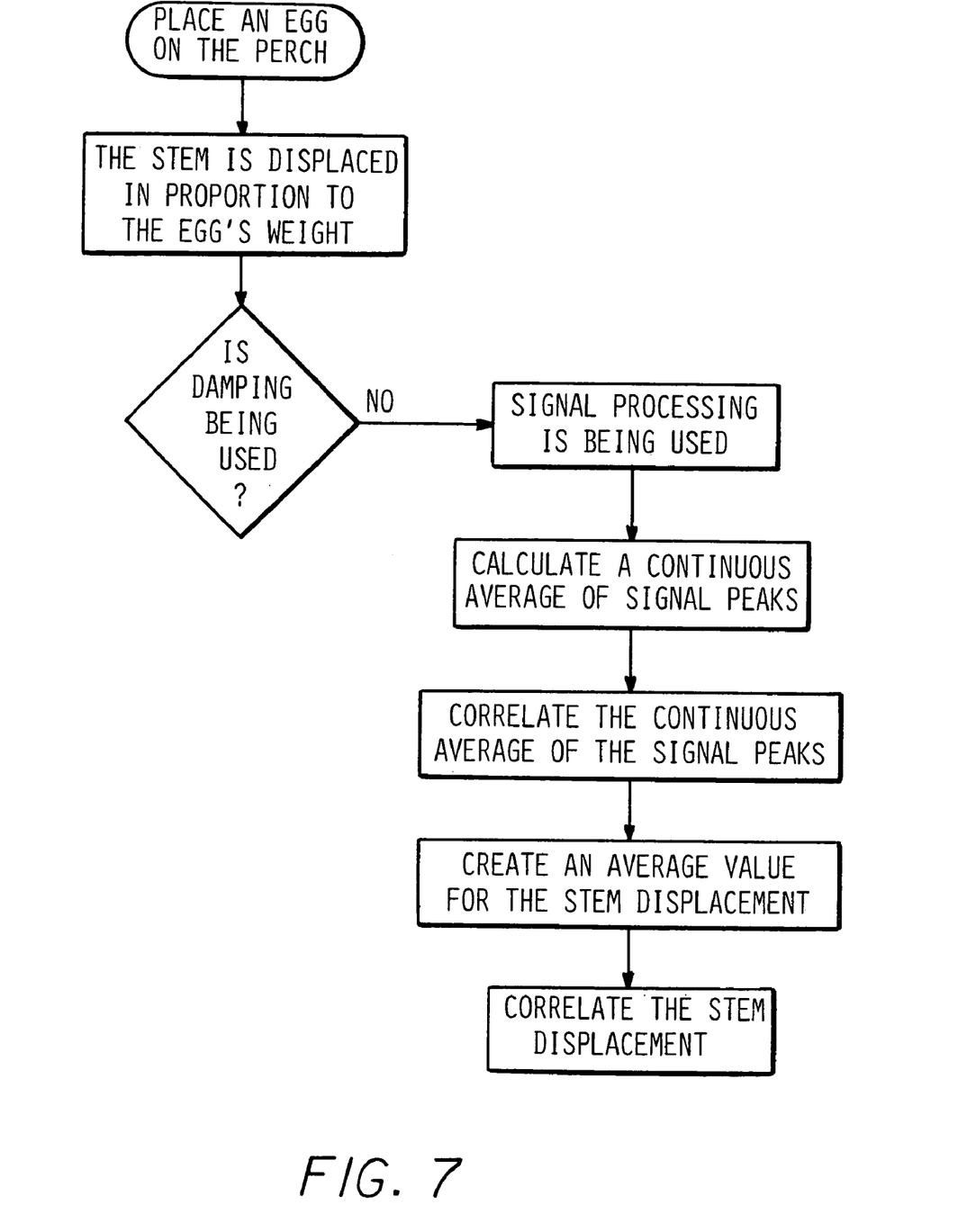
FIG. 7 is a flowchart depicting an optional signal processing aspect of the present invention.

The housing 22 surrounds a control means 22A, shown in phantom in FIG. 6, which forms the basis for the weighing operation of each egg 32. The control means 22A may comprise a suitable control means 22A, such as a central processing unit operating a control program stored in memory as well as associated electronic circuits, analog/digital converters, signal conditioning circuits, etc. One or more connectors 34, 36 and 38 may be provided on the housing 22 to provide connection to external circuits, for supplying electric power to the control means 22A, as well as to output a signal or signals containing the weight of each egg 32.

Although the sensor means 26 may be one of a number of different types of precision sensors, by example only, the sensor means 26 is a transducer which has one or more strain gauges mounted on thin, flexible webs 40 and 42. The webs 40 and 42 are supported in a block 44 which is secured by suitable fasteners, such as by screws 46, to the base or housing 22 and by fasteners, such as screws 48, to a force transmission means or member 50.

Figure 5:
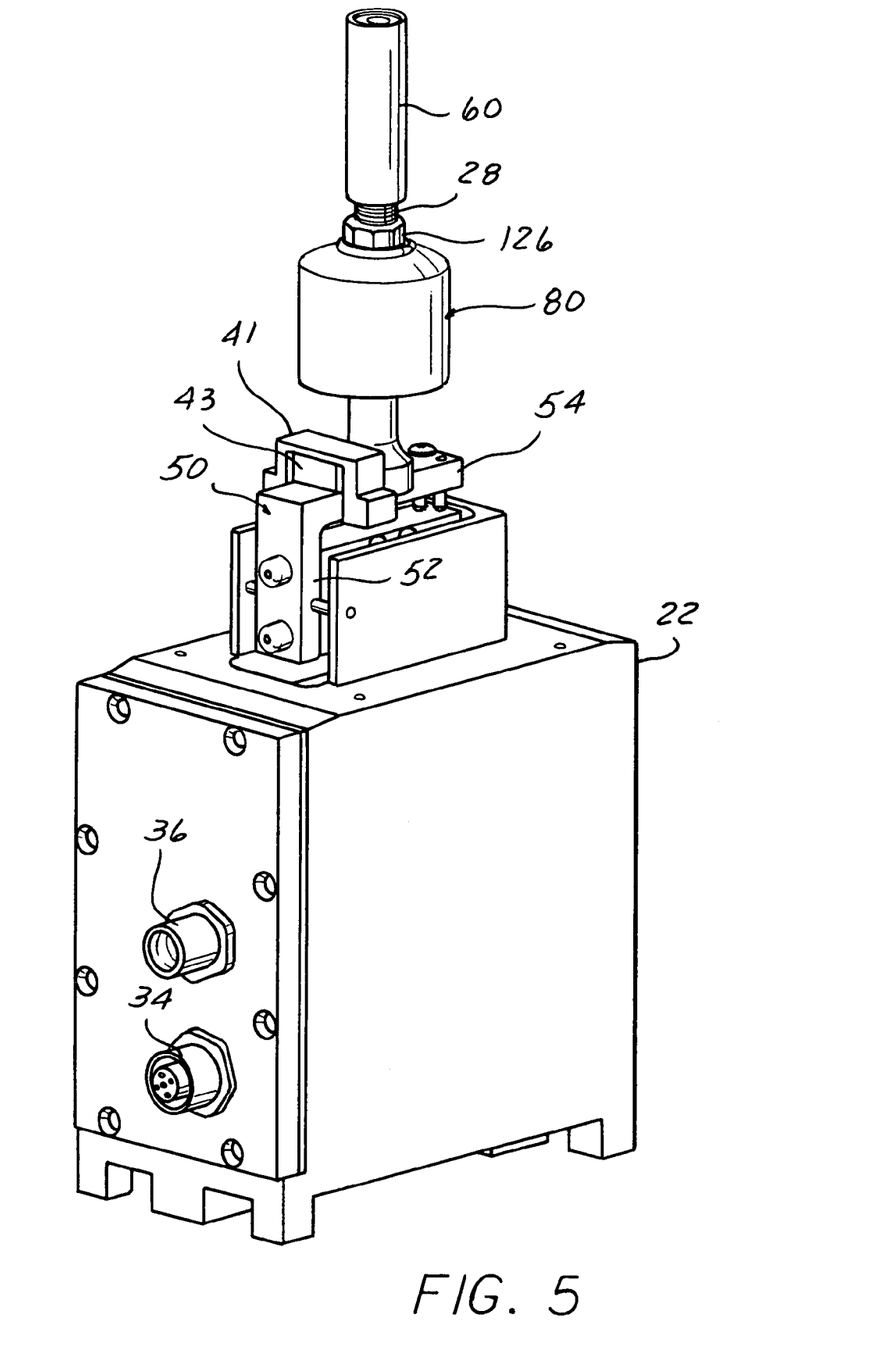
FIG. 5 is a perspective view of an egg weighing apparatus depicting a tuned dynamic vibration absorber formed by attaching a mass to a force transmission member.

In this aspect of the invention, the force transmission member 50 is formed of a solid body, having a generally L-shape, with one leg 52 carrying bores for receiving the fasteners 48 therethrough, and an angularly disposed second leg 54 which has a bore 56 for receiving a fastener, such as a screw, not shown, to attach the transmission member 50 to one end of the stem 28 as shown in FIG. 5. Attached on the top edge of the force transmission member 50 adjacent to the stem 28 is a mass element 41. The attachment of the mass element 41 serves the function of diminishing vibratory oscillation of the perch 30 by minimizing movement of the stem 28. The mass element 41 can be formed from a number of different types of material such as stainless steel, aluminum, tin, etc. The mass element 41 can be attached to the force transmission member 50 via a foam adhesive 43, for example, that behaves as a spring and provides damping. The combination of a mass element 41 and foam adhesive 43 results in the generation of a tuned vibration dynamic absorber.

An alternate tuned dynamic absorber can be formed by suspending a mass element 41 between springs 81 and 83 within a closed chamber 41A containing a viscous fluid as shown in FIG. 6. The chamber 41A is sealed with an o'ring or other suitable sealing means. Such an arrangement protects against chemical exposure and lasts for an infinite duration of time.

The stem 28 is a solid body formed of metal or high strength plastic and having a generally tubular configuration extending between one end 58 joined to the leg 54 of the force transmission member 50 and an opposed second end 60 joined by a fastener, not shown, to the perch 30.

The stem 28 has an intermediate shoulder 62 as well as a threaded end portion 64 for attaching the perch 30 extending from the upper end 60 of the stem 28.

In operation, an egg 32 deposited on the perch 30 will cause a displacement of the stem 28 in proportion to the weight of the egg 32. This displacement will generate distortion of the leg 54 of the force transmission member 50 relative to the opposed leg 52 which will generate a measurable strain in the strain gauges mounted on the webs 40 and 42. The strain gauges which may be two strain gauges on each web 40 and 42, are connected in a Wheatstone bridge circuit, the output of which is supplied to the control means 22A in the base 22 in the form of a signal proportional to the displacement of the stem 28 which is proportional to the weight of the egg 32.

The stem 28 should move freely through the open end 70 of an end collar 72 of the tower 24 so as to have a displacement precisely proportional to the weight of the egg 32 in the perch 30. This requires a small clearance or gap between the outer surface of the stem 28 and the inner surface 74 of the bore extending through the sleeve 72 of the tower 24. This gap must be closed to the external environment to prevent the entry of water or fluid typically employed during a cleaning operation.

To provide a seal, and at the same time, a seal which is resistant to the application of high pressure cleansing fluids, the present invention uniquely utilizes a sealing cap 80 which is releasably mounted on the stem 28. As shown in greater detail in FIG. 2, the collar 72 of the tower 24 is formed with at least one and preferably two or more annularly extending, axially spaced ribs or flanges 82 and 84. The sealing cap 80 is formed of a suitable water resistant, easily formed material. Although metals, such a stainless steel may be employed, in one example of the present cap 80, the cap 80 is formed of a polymeric material, such as Delrin.

The sealing cap 80 is formed of a generally tubular shape having a first end 86, an opposed second end 88, and a sidewall 90 extending between the first and second ends 86 and 88. A portion of the sidewall 90 adjacent the first end 86 may be tapered or formed as a conical surface 92 for weight reduction. An annular recess 94 is formed in the first end 86 adjacent to a bore 96 extending through the first end 86 of the cap 80.

The small diameter bore 96 extending through the first end 86 transitions into a larger bore denoted by reference number 100. The bore 100 is formed with a configuration generally complementary to the exterior shape of the collar 72 of the tower 24 to form a labyrinth or serpentine path from an enlarged diameter aperture or opening 102 at the second end of the cap 100 to a closed inner end 104 at an opposite end of the bore 100.

The cap 100 is formed with axially spaced, alternating smaller and larger diameter cavities 106, 108, 110, 112, and 114 extending axially from the first opening 102 to the opposed end 104 of the bore 100. The smaller diameter cavities 108 and 112, which may be as few as one and preferably two or more, by example only, are formed by annular flanges 116 and 118 which extend radially inward from the sidewall 90 of the cap 100.

As shown in FIG. 2, the larger diameter and larger volume cavities 106 and 110 are concentric with the annular flanges 82 and 84, respectively, on the collar 72 of the tower 24. The smaller diameter and smaller volume cavities 108 and 110 are disposed adjacent to and axially spaced from the flanges 82 and 84. In conjunction with the radially inward extending end flange 120 which forms the aperture 102 in the second end 88 of the cap 100, as can be clearly seen in FIG. 2, the bore 100 defines a labyrinth or serpentine shaped path from the aperture 102 to the opposed closed end 104 which is disposed adjacent to the upper end of the gap between the outer surface of the stem 28 and the inner surface 72 of the collar 72 of the tower 24. This labyrinthian path blocks the entry of cleaning fluids, such as water, through the aperture 102 for any significant axial distance along the length of the bore 100 thereby preventing the entry of such cleaning solutions through the opening in the end 70 of the collar 72 into the gap between the stem 28 and the collar 72.

In this manner, the sealing cap 80 of the present invention uniquely enables the egg weighing apparatus 20 to accurately weigh eggs and, at the same time, to be rapidly and efficiently cleaned using cleaning solution applied with a high pressure.

The sealing cap 80 is fixedly mounted on the stem 28 by means of a fastener, such as an internally threaded nut 126 which is threaded over external threads 128 formed on the end portion of the stem 28. A metal or plastic washer 130 may be employed with the nut 126. A sealing member, such an O-ring 132, is mounted in the recess 94 to seal the connection between the stem 28 and the cap 80. In this manner, the cap 80 is unitarily mounted on the stem 28 and moves with deflection of the stem 28 when an egg 32 is introduced into the perch 30.

Figure 3:
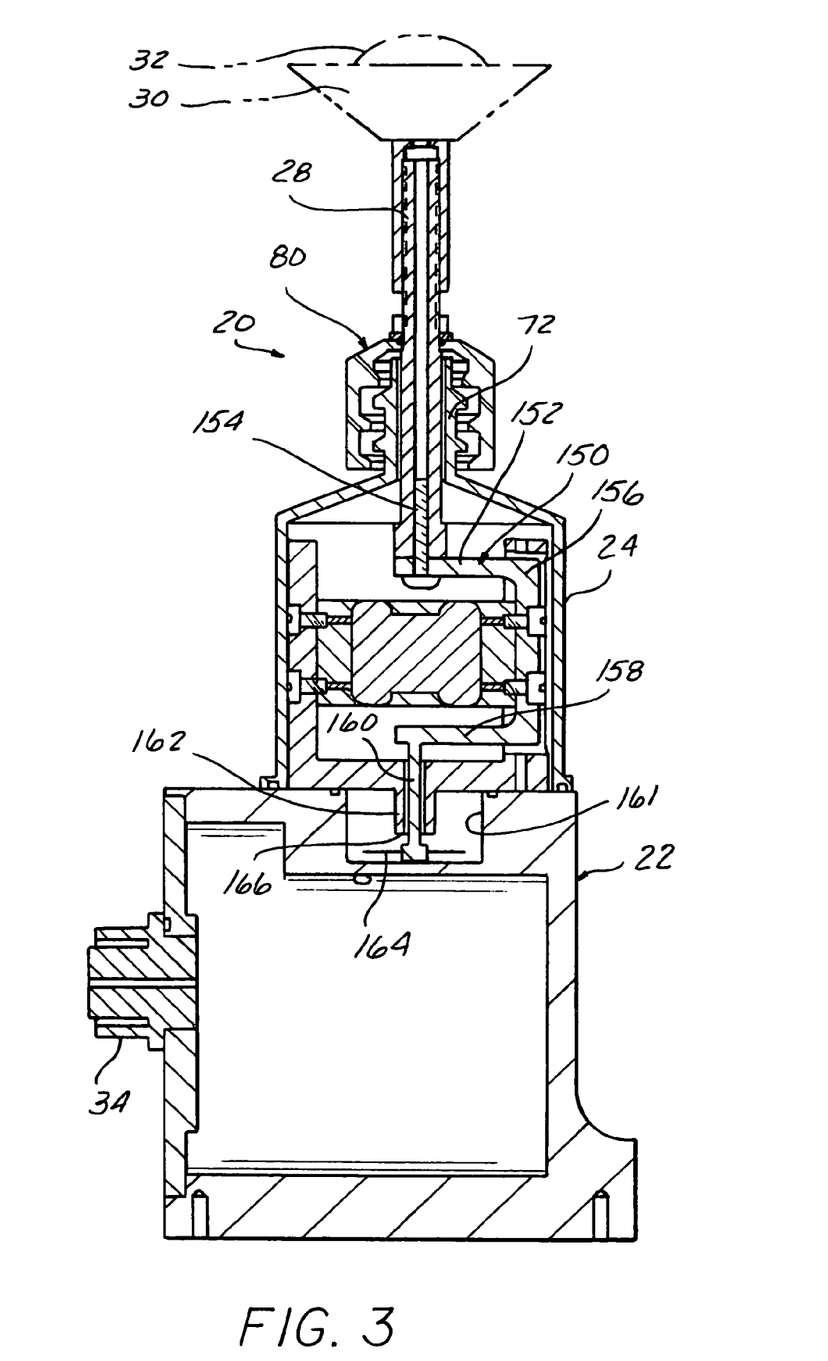
FIG. 3 is a cross sectional view of an egg weighing apparatus according to another aspect of the present invention.

Turning now to FIG. 3, there is depicted a modification to the egg weighing apparatus 20. This aspect of the apparatus 20 includes dampening of deflection or movement of the stem 28 when an egg 32 is deposited on one end. In this aspect, a force transmitting member 150, having a generally U-shape formed of a first end leg 152 fixed by means of a threaded fastener 154 to one end of the stem 28, extends angularly from an intermediate leg 156. An opposed second leg 158 extends angularly from the intermediate leg 156. A shaft 160 extends from one end of the second leg 158 into a recess or well 161 formed in the upper end of the base 22. The shaft 160 slidably extends through a larger diameter shaft 162 formed as part of the tower 24. The shaft 160 is spaced by a small gap from the inner surface of the bore in the shaft 162.

A disk 164 is carried on one end of the shaft 160 and is positioned in the bottom of the recess or well 161. The well 161 will be filled with a suitable damping material, such as silicone, which fills the well 161 to a height below the end 166 of the shaft 162 to prevent the entry of the silicone or other fluid into the gap between the shaft 160 and the shaft 162.

The weight of an egg 32 deposited on one end of the stem 28 will cause deflection of the stem 28, the force transmitting member 150 and the disk 164. Oscillation of the shaft 160 caused by such deflection will be dampened by dampening material surrounding the disc 164 which has a much larger surface area than the cross section of the shaft 160.

One feature of this construction is that no separate, mechanical sealing means is required to maintain the damping fluid within the recess 160. The damping fluid flows like water such that any tilting of the base 22 from its normal mounting position shown in the orientation shown in FIG. 3 will immediately cause the damping fluid to flow to one side or the other of the well 161 away from the end 166 of the shaft 162. This prevents entry of the damping fluid into the gap between the shaft 162 and the shaft 160.

Even if the entire weighing apparatus 20 was inverted, such as prior to mounting in a fixed position in an egg handling system, the damping fluid would quickly flow to one or both sides of the shaft 162 before it could enter the opening at the end 166 of the shaft 162.

Thus, the use of the well or recess 160 eliminates the need of a seal which could cause seal friction and result in measurement error.

FIG. 6 illustrates the aspect of the apparatus 20 that includes dampening movement of the stem 28 when an egg 32 is deposited on one end. In this aspect, the mass element 41 is located upon a bottom spring 83 that is attached to the force transmission member 50 and the mass element 41. At the top of the mass element 41 is another spring 81 that is attached to the mass element 41 and the stem 28. The cavity 41A may contain fluid used to damp the motion of the mass element 41 with respect to the stem 28 motion. Together, the mass element 41, the springs 81 and 83 and the fluid in the cavity 41A form a tuned dynamic vibration absorber that serves the function of diminishing vibratory oscillation of the egg scale perch 30 by minimizing movement of the stem 28.

Figure 4:
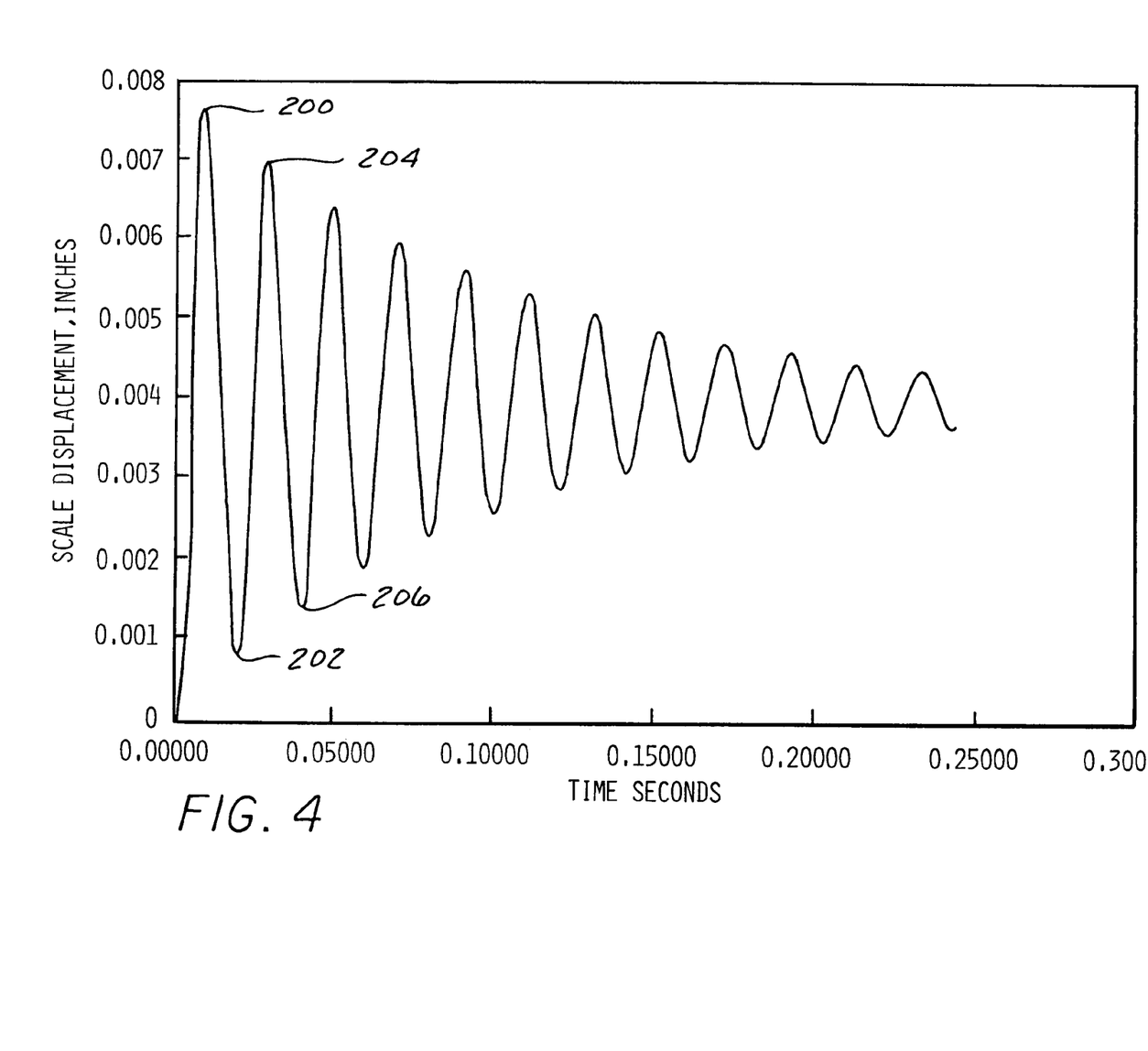
FIG. 4 is a graph depicting the output of an egg weighing apparatus starting from the application of an egg to the weighing platform.

Referring now to FIG. 4, there is illustrated a pictorial representation of the displacement of the stem 28 from the instant an egg 32 is deposited on the perch 30. As can be clearly seen in FIG. 4, the displacement of the stem 28 exhibits oscillations due to the momentum of the egg as it contacts the perch 30 as well as further movement of the egg 32 on the perch 30 due to the typical non-roundness of an egg.

As shown in FIG. 4, an offset of 0.004 inches is preset into the apparatus 20. The stem 28 will settle at this displacement without any weight being applied to the perch 30 at one end of the stem 28.

When an egg 32 is deposited on the perch 30, the displacement of the stem 28 rapidly increases to a first peak magnitude 200, then transitions to a first valley magnitude 202 before returning to a second peak magnitude 204, less than the first peak magnitude 200, and continuing as the oscillations asymptotically or exponentially die off with decreasing magnitude.

The typical prior art egg weighing apparatus would normally wait until the oscillations reach a minimal value before executing a weighting operation. However, this is time consuming.

According to this aspect of the present invention, signal processing in lieu of complete mechanical damping is employed. The magnitude of the first peak 200 and the magnitude of the first valley 202 are first measured and then averaged. A continuing average is then made with the second peak magnitude 204 and the following second valley 206 to further refine the cumulative average. These averages of each peak and valley pair, such as peak and valley pair 200 and 202 and peak or valley pair 204 and 206, can be integrated over a predetermined measurement time period to create an average value for the stem displacement which is proportional to the weight of the egg 32 on the perch 30 on one end of the stem 28. This displacement can be correlated through a lookup table or other means to a known weight of the egg 32. Thus, the stem 28 displacement measured by the transducer 26 can generate an output signal used to precisely measure the weight of the egg 32 in only a few oscillations thereby significantly reducing the time for making an accurate measurement of the weight of an egg 32 to further increase production efficiency.

The above described averaging technique can be implemented digitally, as described above, or in a combined analog and digital manner. In an analog calculation, the instant that an egg 32 is deposited on the stem 28 a settle time which can last for a predetermined time, such as 50 to 60 milliseconds, is timed. At the conclusion of the settle time, the stem displacement is measured by an analog filter which has the effect of creating a continuing average between alternating peaks and valleys in the oscillating displacement signal. This analog output can be integrated over time by digital processing circuitry or in a central processing unit to generate a digital average signal which is proportional to the weight of the egg 32.

What is claimed is:

1. An apparatus for weighing an egg comprising:
   a housing including a controller for weighing an egg in a weighing platform;
   a sensor for weighing an egg including a transducer having at least one strain gauge secured to a force transmission member, the force transmission member formed of a solid body with two legs, a first leg carrying bores for receiving fasteners for attaching the transmission member to the transducer, and an angularly disposed second leg attaching the transmission member to a stem;
   a tower mounted on the housing for supporting and surrounding the sensor;
   the stem movably displaced through one open end of the tower and
   supporting the weighing platform; and a tuned dynamic absorber attached to the force transmission member.

2. An apparatus for weighing an egg comprising:
   a housing including a controller for weighing an egg in a weighing platform;
   a sensor for weighing an egg including a transducer having at least one strain gauge secured to a force transmission member, the force transmission member formed of a solid body with two legs, a first leg carrying bores for receiving fasteners for attaching the transmission member to the transducer, and an angularly disposed second leg attaching the transmission member to a stem;
   a tower mounted on the housing for supporting and surrounding the sensor means;
   the stem movably displaced through one open end of the tower and supporting the weighing platform, wherein one end of the stem joined to the second leg of the transmission member and the other end of the stem joined to the weighing platform; and
   a sealing cap releasably mounted on the outer surface of the stem between the tower and the egg weighing platform.

3. The apparatus of claim 2 further comprising a seal member for sealing connection between the sealing cap and the stem.

4. The apparatus of claim 2 wherein the sealing cap comprises a bore and the cap has a first end and a second end.

5. The apparatus of claim 2 further comprising a collar formed with at least one annularly extending, axially spaced flange.

6. The apparatus of claim 4 wherein the sealing cap bore has a complimentary shape to the exterior shape of the collar, forming a labyrinth path through the second end of the cap.

7. The apparatus of claim 4 wherein the cap is formed with axially spaced, alternating small and large diameter cavities.

8. The apparatus of claim 4 wherein the cap has at least one small diameter cavity formed of annular flanges.

9. The apparatus of claim 8 wherein the cap has at least one large diameter cavity concentric with the annular flange on the collar to block entry of fluid into a collar.

10. The apparatus of claim 2 further comprising a disk carried on one end of the stem shaft and positioned in the bottom of a recess.

11. The apparatus of claim 2 wherein the recess is filled with a viscous dampening material to dampen stem movement.

12. The apparatus of claim 8 further comprising:
    means for placing an egg in a weighing platform;
    means for displacing a stem connected to the weighing platform in proportion to the weight of the egg wherein such displacement generates distortion of a weight transmission member coupled to the stem resulting in a measurable strain; and
    means for applying the measured strain to a control means in the form of a signal proportional to the displacement of the stem.

13. The apparatus of claim 2 further comprising means for calculating a continuous average of signal peaks.

14. The apparatus of claim 2 further comprising means for correlating the continuous average of the signal peaks and creating an average value for the stem displacement.

15. The apparatus of claim 2 further comprising means for correlating the stem displacement.

16. The apparatus of claim 2 further comprising means for calculating a continuous average of signal peaks.

17. The apparatus of claim 2 further comprising means for correlating the continuous average of the signal peaks and creating an average value for the stem displacement.

18. The apparatus of claim 1, wherein the tuned dynamic absorber comprises:
    a mass element; and
    at least one spring suspending the mass element.

* * * * *